US011812973B2

(12) United States Patent
Sieh et al.

(10) Patent No.: US 11,812,973 B2
(45) Date of Patent: Nov. 14, 2023

(54) SHEATHED SURGICAL SAW BLADE WITH BEARINGS

(71) Applicant: Conmed Corporation, Utica, NY (US)

(72) Inventors: John Sieh, Safety Harbor, FL (US); David Gonzalez, Apollo Beach, FL (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 16/977,345

(22) PCT Filed: Mar. 5, 2019

(86) PCT No.: PCT/US2019/020677
§ 371 (c)(1),
(2) Date: Sep. 1, 2020

(87) PCT Pub. No.: WO2019/173285
PCT Pub. Date: Sep. 12, 2019

(65) Prior Publication Data
US 2021/0100561 A1  Apr. 8, 2021

Related U.S. Application Data

(60) Provisional application No. 62/724,914, filed on Aug. 30, 2018, provisional application No. 62/639,040, filed on Mar. 6, 2018.

(51) Int. Cl.
*A61B 17/14* (2006.01)
*A61B 17/56* (2006.01)
*A61B 17/00* (2006.01)

(52) U.S. Cl.
CPC ............ *A61B 17/142* (2016.11); *A61B 17/56* (2013.01); *A61B 2017/0084* (2013.01)

(58) Field of Classification Search
CPC ........ A61B 17/14; A61B 17/142; A61B 17/15
See application file for complete search history.

(56) References Cited

U.S. PATENT DOCUMENTS

| 2,854,981 A | 10/1958 | Marshal |
| 4,617,930 A | 10/1986 | Saunders |
(Continued)

FOREIGN PATENT DOCUMENTS

| DE | 2935732 | 3/1981 |
| DE | 202008017023 | * 3/2009 |
(Continued)

OTHER PUBLICATIONS

International Search Report Form PCT/ISA/220, International Application No. PCT/US19/20677, pp. 1-14, dated Jun. 11, 2019.
(Continued)

*Primary Examiner* — Larry E Waggle, Jr.
(74) *Attorney, Agent, or Firm* — BOND, SCHOENECK & KING, PLLC; Frederick Price

(57) ABSTRACT

A sheathed blade assembly for minimizing or preventing contact between the moving interior blade and the exterior sheath. The assembly includes an exterior sheath having a first portion and second portion with an inner lumen therebetween, an interior blade movable within the inner lumen of the exterior sheath, a first pocket within a first surface of the interior blade, and a first ball bearing within the first pocket. The first ball bearing creates a clearance amount between the first surface of the interior blade and the first portion of the exterior sheath. The assembly may also include a second pocket within a second surface of the interior blade for a second ball bearing. The second ball bearing creates a clearance amount between the second surface of the interior blade and the second portion of the
(Continued)

exterior sheath. The second pocket is in a staggered configuration relative to the first pocket.

18 Claims, 10 Drawing Sheets

(56) References Cited

U.S. PATENT DOCUMENTS

| | | | |
|---|---|---|---|
| 5,014,430 A | | 5/1991 | Wortham |
| 5,087,261 A | | 2/1992 | Ryd et al. |
| 5,122,142 A | | 6/1992 | Pascaloff |
| 5,133,728 A | | 7/1992 | Petersen |
| 5,135,533 A | | 8/1992 | Petersen et al. |
| 5,178,626 A | | 1/1993 | Pappas |
| 5,263,972 A | * | 11/1993 | Evans .................. B23D 51/10 606/176 |
| 5,306,285 A | | 4/1994 | Miller et al. |
| 5,366,312 A | | 11/1994 | Raines |
| 5,382,249 A | | 1/1995 | Fletcher |
| 5,403,318 A | | 4/1995 | Boehringer et al. |
| 5,439,472 A | | 8/1995 | Evans et al. |
| 5,489,285 A | | 2/1996 | Goris |
| 5,496,316 A | | 3/1996 | Goris |
| 5,507,763 A | | 4/1996 | Petersen et al. |
| 5,554,165 A | | 9/1996 | Raitt et al. |
| 5,569,257 A | | 10/1996 | Arnegger et al. |
| 5,725,530 A | | 3/1998 | Popken |
| 5,735,866 A | | 4/1998 | Adams et al. |
| 5,768,933 A | | 6/1998 | Tanner et al. |
| 5,839,196 A | | 11/1998 | Trott |
| 5,846,244 A | | 12/1998 | Cripe |
| 6,022,353 A | | 2/2000 | Fletcher et al. |
| 6,106,535 A | | 8/2000 | Dross et al. |
| 6,113,618 A | | 9/2000 | Nic |
| 6,503,253 B1 | | 1/2003 | Fletcher et al. |
| 6,684,481 B2 | | 2/2004 | Michael |
| 6,723,101 B2 | | 4/2004 | Fletcher et al. |
| 6,875,222 B2 | | 4/2005 | Long et al. |
| 6,896,679 B2 | | 5/2005 | Danger et al. |
| 7,001,403 B2 | | 2/2006 | Hausmann et al. |
| 7,189,239 B2 | | 3/2007 | Fisher et al. |
| 7,497,860 B2 | | 3/2009 | Carusillo et al. |
| 7,527,628 B2 | | 5/2009 | Fletcher et al. |
| 7,691,106 B2 | * | 4/2010 | Schenberger ........ A61B 17/142 606/82 |
| 7,704,253 B2 | | 4/2010 | Bastian et al. |
| 7,704,254 B2 | | 4/2010 | Walen |
| 7,744,616 B2 | | 6/2010 | O& et al. |
| 8,043,292 B2 | | 10/2011 | Carusillo |
| 8,348,951 B2 | | 1/2013 | Walen et al. |
| 8,444,647 B2 | | 5/2013 | Walen et al. |
| 8,449,550 B2 | | 5/2013 | Talamini |
| 8,486,560 B2 | | 7/2013 | Tartaglia |
| 8,608,745 B2 | | 12/2013 | Guzman et al. |
| 8,672,943 B2 | | 3/2014 | Fisher et al. |
| 8,696,673 B2 | | 4/2014 | Walen et al. |
| 8,702,710 B2 | | 4/2014 | Carusillo |
| 8,920,424 B2 | | 12/2014 | Boykin |
| 8,936,597 B2 | | 1/2015 | Wang et al. |
| 8,966,772 B2 | | 3/2015 | Legrand et al. |
| 9,060,783 B2 | | 6/2015 | Walen et al. |
| 9,072,526 B2 | | 7/2015 | Carusillo |
| 9,439,655 B2 | | 9/2016 | Cosgrove et al. |
| 10,687,824 B2 | * | 6/2020 | Shiels .................. A61B 17/142 |
| 2003/0014067 A1 | | 1/2003 | Kullmer et al. |
| 2004/0098000 A1 | | 5/2004 | Kleinwaechter |
| 2004/0243136 A1 | | 12/2004 | Gupta et al. |
| 2005/0245935 A1 | | 11/2005 | Casey et al. |
| 2007/0073303 A1 | | 3/2007 | Namba |
| 2008/0027449 A1 | | 1/2008 | Gundlapalli et al. |
| 2008/0119860 A1 | | 5/2008 | McCarthy |
| 2009/0093815 A1 | | 4/2009 | Fletcher et al. |
| 2017/0348007 A1 | * | 12/2017 | Shiels .................. A61B 17/142 |
| 2021/0100561 A1 | | 4/2021 | Sieh et al. |

FOREIGN PATENT DOCUMENTS

| | | | |
|---|---|---|---|
| DE | 202008017023 U1 | * 3/2009 | ........... A61B 17/142 |
| DE | 202008017023 U1 | 3/2009 | |
| DE | 202008017026 | 3/2009 | |
| DE | 102008063239 | 6/2010 | |
| DE | 102008063239 A1 | * 6/2010 | ........... A61B 17/142 |
| EP | 1880682 | 2/2008 | |
| EP | 1882538 | 1/2009 | |
| EP | 3761890 A1 | 1/2021 | |
| KR | 20080059191 | 6/2008 | |
| WO | 2004/105623 | 12/2004 | |
| WO | 2019173285 A1 | 9/2019 | |

OTHER PUBLICATIONS

European Search Report, App. No. 21171901.8, dated Oct. 15, 2021, pp. 1-8.
KR Office Action, App. No. 10-2020-7025073, dated Mar. 29, 2022, pp. 1-10.
JP Office Action, App. No. 2020-545634, dated Jun. 14, 2022, pp. 1-10.
CA Office Action, App No. 3,091,362, dated Apr. 5, 2023, pp. 1-4.

* cited by examiner

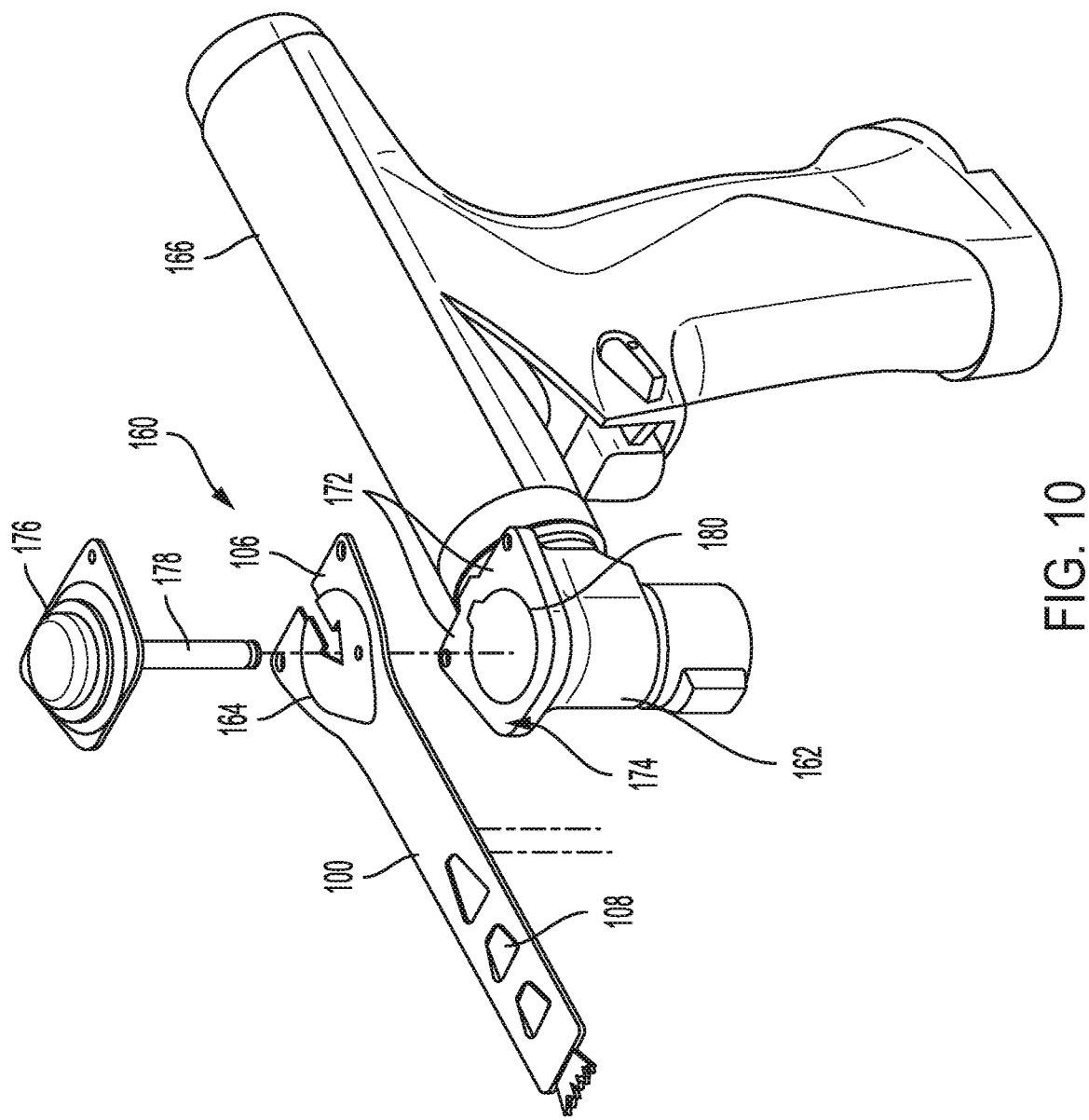

SHEATHED SURGICAL SAW BLADE WITH BEARINGS

CROSS-REFERENCE TO RELATED APPLICATIONS

CROSS-REFERENCES TO RELATED APPLICATIONS

This application is a national stage application under 35 U.S.C. 371 based on international patent application PCT/US19/20677 filed on Mar. 5, 2019, which claims priority to U.S. Provisional Patent Application Ser. No. 62/639,040, filed on Mar. 6, 2018 and U.S. Provisional Patent Application Ser. No. 62/724,914 filed on Aug. 30, 2018, the entireties of which are incorporated herein by reference.

BACKGROUND OF THE INVENTION

1. Field of the Invention

The present invention is directed generally to a surgical blade assembly and, more particularly, to a sheathed blade assembly with a clearance amount between the exterior sheath and the interior blade to minimize wear.

2. Description of Related Art

Surgical sheathed blades comprise of a moving inner member (blade) and an outer stationary member (sheath). During use, contact between the moving and stationary members is inevitable as cantilever forces are applied to the assembly that cause the moving and stationary parts to come into contact. Because of the high linear speed of the blade, the assembly can get very hot and wear when the blade comes in contact with the stationary sheath. The heating of the sheath and blade can cause bone necrosis as well as patient or user injury. Furthermore, wear created by the blade contacting the sheath will generate metal particulate that may fall into the surgical site.

By design, a sheathed blade assembly and non-sheathed (standard) blades require different mechanisms to interface with a surgical saw handpiece, thus necessitating different handpieces to actuate one blade or the other. The need for two different saw handpieces, one that drives sheathed blade assemblies and one that drives non-sheathed blade imposes additional costs to the surgical facility and/or the need to choose one blade option (sheathed or non-sheathed).

Therefore, there is a need for a single surgical saw handpiece for driving both sheathed blade assemblies as well as non-sheathed (standard) blades, and a sheathed blade assembly that prevents or minimizes potential contact between the inner moving blade and the sheath.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

The present invention is directed to a single surgical saw that will drive both sheathed blade assemblies as well as non-sheathed (standard) blades, and a sheathed blade that prevents the potential contact between the moving interior blade and the exterior sheath. According to one aspect, the sheathed blade assembly includes an exterior sheath having a top portion and a bottom portion with an inner lumen therebetween, an interior blade movable within the inner lumen of the exterior sheath, and at least one ball bearing within the inner lumen of the exterior sheath. The ball bearing creates a clearance amount between the interior blade and at least one of the top portion and the bottom portion of the exterior sheath.

According to another aspect, the sheathed blade assembly includes an exterior sheath having a first portion and a second portion with an inner lumen therebetween, an interior blade movable within the inner lumen of the exterior sheath, a first pocket within a first surface of the interior blade, and a first ball bearing within the first pocket. The first ball bearing creates a clearance amount between the first surface of the interior blade and the first portion of the exterior sheath.

According to another aspect, the present invention is a surgical saw. The surgical saw includes a saw head comprising a collet with an opening configured to receive a movable blade. The blade is removably connected within the collet. A handpiece is connected to the saw head and the handpiece has a drive mechanism which moves the blade.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

FIG. 10 is an exploded view schematic representation of the sheathed blade assembly connected to the universal saw head of FIG. 8.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
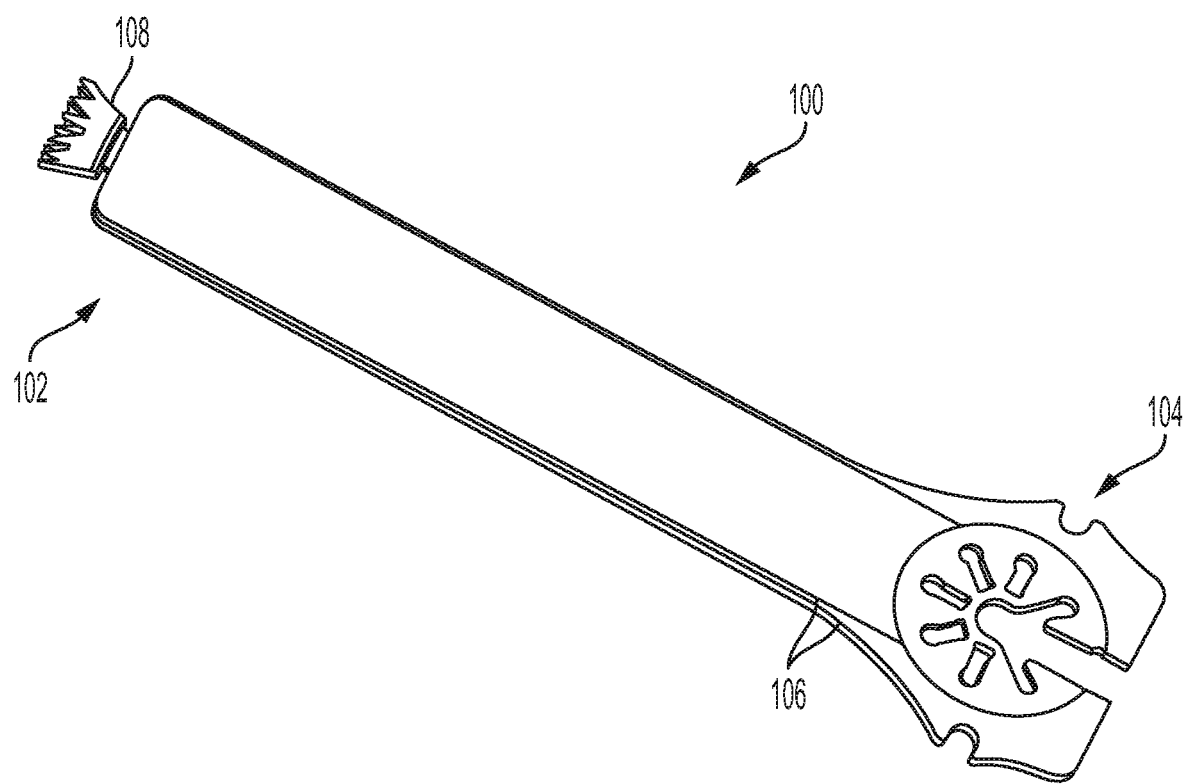
FIG. 1 is a top perspective view schematic representation of a sheathed blade assembly, according to an embodiment.

Referring now to the figures, wherein like reference numerals refer to like parts throughout, FIG. 1 shows a top perspective view schematic representation of a sheathed blade assembly 100, according to an embodiment. The sheathed blade assembly 100 extends from a proximal end 102 to a distal end 104. As shown in the depicted embodiment, the sheathed blade assembly 100 comprises a stationary exterior sheath 106 with a movable interior blade 108 extending therefrom.

Figure 2:
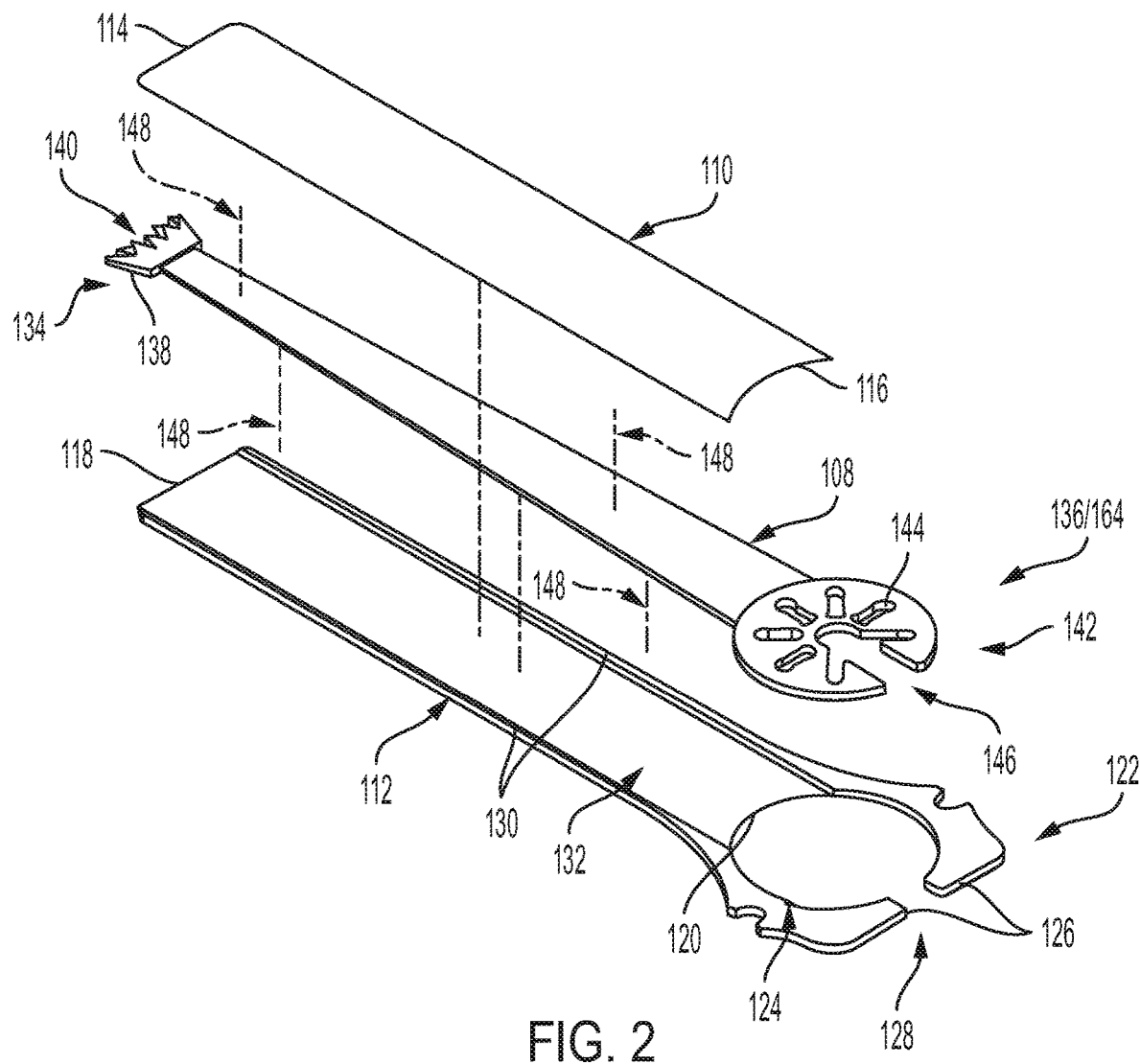
FIG. 2 is an exploded perspective view schematic representation of the sheathed blade assembly, according to an embodiment.

Turning now to FIG. 2, there is shown an exploded perspective view schematic representation of the sheathed blade assembly 100, according to an embodiment. In the depicted embodiment, the sheathed blade assembly 100 comprises an exterior sheath 106 having two parts, a top portion 110 and a bottom portion 112. The top portion 110 and the bottom portion 112 are composed of metal, such as stainless steel. As shown in FIG. 2, the top portion 110 is an elongated, rectangular plate. In the depicted embodiment, the top portion 110 has a straight proximal edge 114 and a curved distal edge 116. The bottom portion 112 is also an elongated, rectangular plate with a straight proximal edge 118 and a curved distal edge 120. The bottom portion 112 also comprises a distal end 122 comprising a circular aperture 124. In the depicted embodiment, the distal end 122 of the bottom portion 112 comprises a pair of arms 126 (or prongs) extending therefrom. The arms 126 extend toward each other but do not meet, forming a gap 128 therebetween. The gap 128 extends into the circular aperture 124, as shown.

Still referring to FIG. 2, the exterior sheath 106 further comprises a track 130 extending along the bottom portion 112 between the straight proximal edge 118 and the curved distal edge 120. The track 130 defines an inner lumen 132 within the sheathed blade assembly 100 between the top portion 110 and the bottom portion 112 of the exterior sheath 106. The inner lumen 132 is sized and configured to fit and accommodate the interior blade 108.

Figure 7:
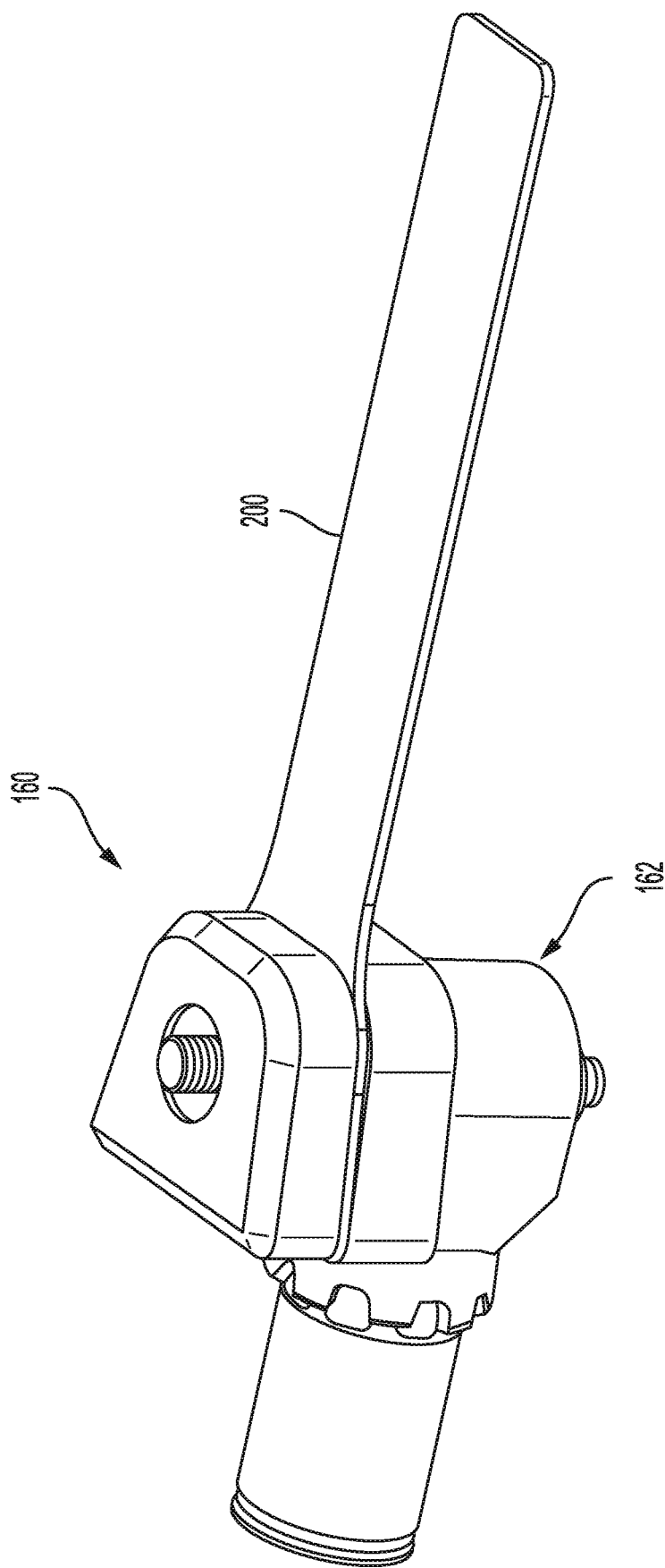
FIG. 7 is a side perspective view schematic representation of a universal saw head, according to an embodiment.

As shown in FIG. 2, the interior blade 108 comprises a proximal cutting end 134 and a distal connecting end 136 (also referred to as the "hub" 164). In the depicted embodiment, the interior blade 108 is elongated and tapered, narrowing towards the proximal cutting end 134. The proximal cutting end 134 of the interior blade 108 comprises a head 138 with a plurality of cutting teeth 140. In the embodiment shown in FIG. 2, the head 138 of the proximal cutting end 134 is trapezoid-shaped, increasing in width in the proximal direction. The distal connecting end 136 comprises a circular disk 142 having a plurality of slots 144 and an opening 146 extending therethrough. The disk 142 is sized and configured to fit within the aperture 124 in the distal end 122 of the bottom portion 112. Further, the opening 146 in the disk 142 is located such that it aligns with the gap 128 in the distal end 122 of the bottom portion 112. The purpose of the distal connecting end 136 of the interior blade 108 and the distal end 122 of the bottom portion 112 is to facilitate connection of the sheathed blade assembly 100 to a saw saw head 160 (FIG. 7).

As also shown in FIG. 2, the sheathed blade assembly 100 additionally comprises one or more ball bearings 148 between the top portion 110 of the exterior sheath 106 and the interior blade 108 and between the bottom portion 112 of the exterior sheath 106 and the interior blade 108. The ball bearings 148 are seated or located on both sides of the interior blade 108 and roll relative to the interior blade 108 and the top and bottom portions 110, 112 of the exterior sheath 106. Thus, the ball bearings 148 permit movement of the interior blade 108 and minimize contact between the interior blade 108 and the exterior sheath 106. The ball bearings 148 can be imbedded in a blind hole or slot (not shown) in the interior blade 108 or in the top and bottom portions 110, 112 of the exterior sheath 106. The ball bearings 148 protrude beyond the surfaces of the interior blade 108 or the exterior sheath 106 in order to maintain clearance between the interior blade 108 and the exterior sheath 106.

Figure 3:
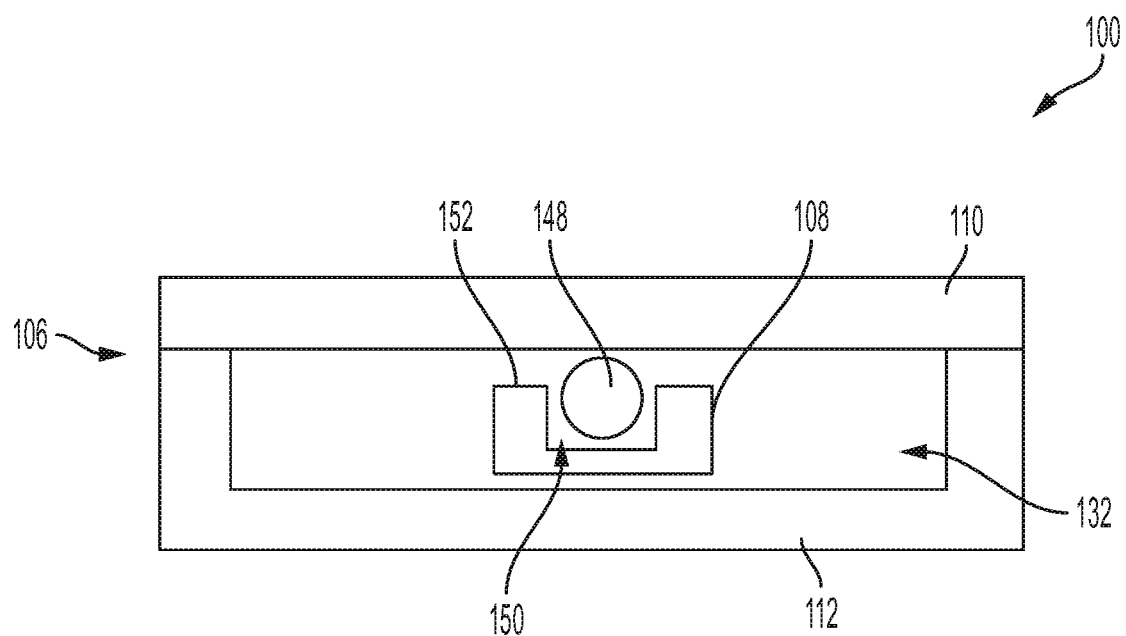
FIG. 3 is a distal view schematic representation of the sheathed blade assembly, according to an embodiment.
Figure 4:
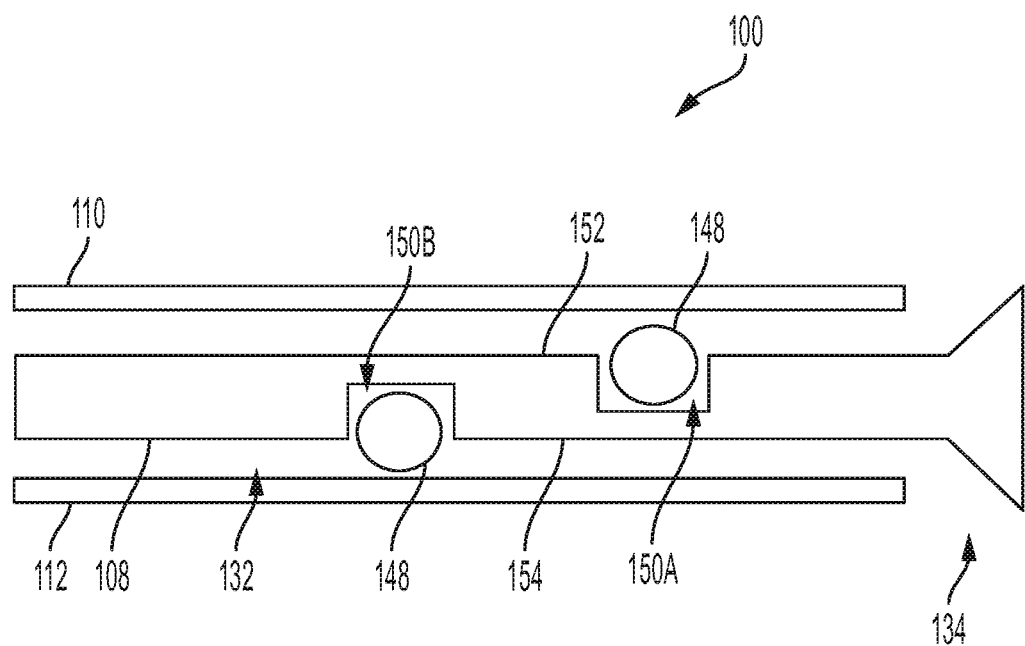
FIG. 4 is a side view schematic representations of the sheathed blade assembly, according to an embodiment.

Referring now to FIGS. 3 and 4, there are shown distal and side views schematic representations of the sheathed blade assembly 100, according to an embodiment. FIG. 3 shows the proximal end 102 of the sheathed blade assembly 100. In the depicted embodiment, the interior blade 108 is shown positioned within the inner lumen 132 of the exterior sheath 106 (between the top portion 110 and the bottom portion 112). As also shown in FIG. 3, the ball bearing 148 is positioned within a pocket 150 in a top surface 152 of the interior blade 108.

FIG. 4 shows a side view of the sheathed blade assembly 100. In the depicted embodiment, the interior blade 108 is positioned within the inner lumen 132 of the exterior sheath 106. The interior blade 108 shown in FIG. 4 has two pockets 150A, 150B, one pocket 150A in the top surface 152 of the interior blade 108 and one pocket 150B in a bottom surface 154 of the interior blade 108, with the ball bearings 148 positioned within the pockets 150A, 150B. In the depicted embodiment, the two pockets 150A, 150B are staggered such that one pocket 150A is distal relative to the proximal cutting end 134 of the interior blade 108 as compared to the other pocket 150B. Although the ball bearings 148 can be sized and configured to fit within the pockets 150A, 150B, the sheathed blade assembly 100 does not require pockets 150A, 150B. The ball bearings 148 can be constrained by the size of the exterior sheath 106 and the width of the interior blade 108 within the exterior sheath 106. The staggered configuration of the ball bearings 148 provides clearance between the interior blade 108 and the exterior sheath 106, greatly reducing the friction within the assembly, thereby reducing heat, wear, and metal particle generation. The clearance also allows fluid to lubricate the moving parts of the sheathed blade assembly 100.

Figure 5:
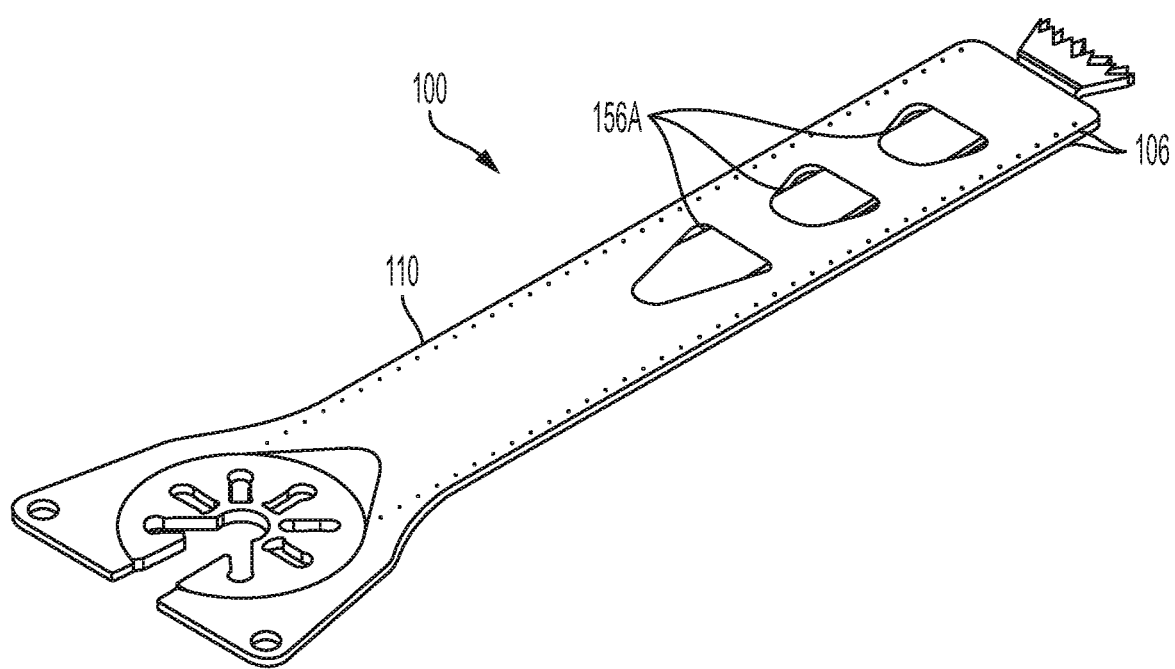
FIG. 5 is a top perspective view schematic representation of a sheathed blade assembly, according to an alternative embodiment.
Figure 6:
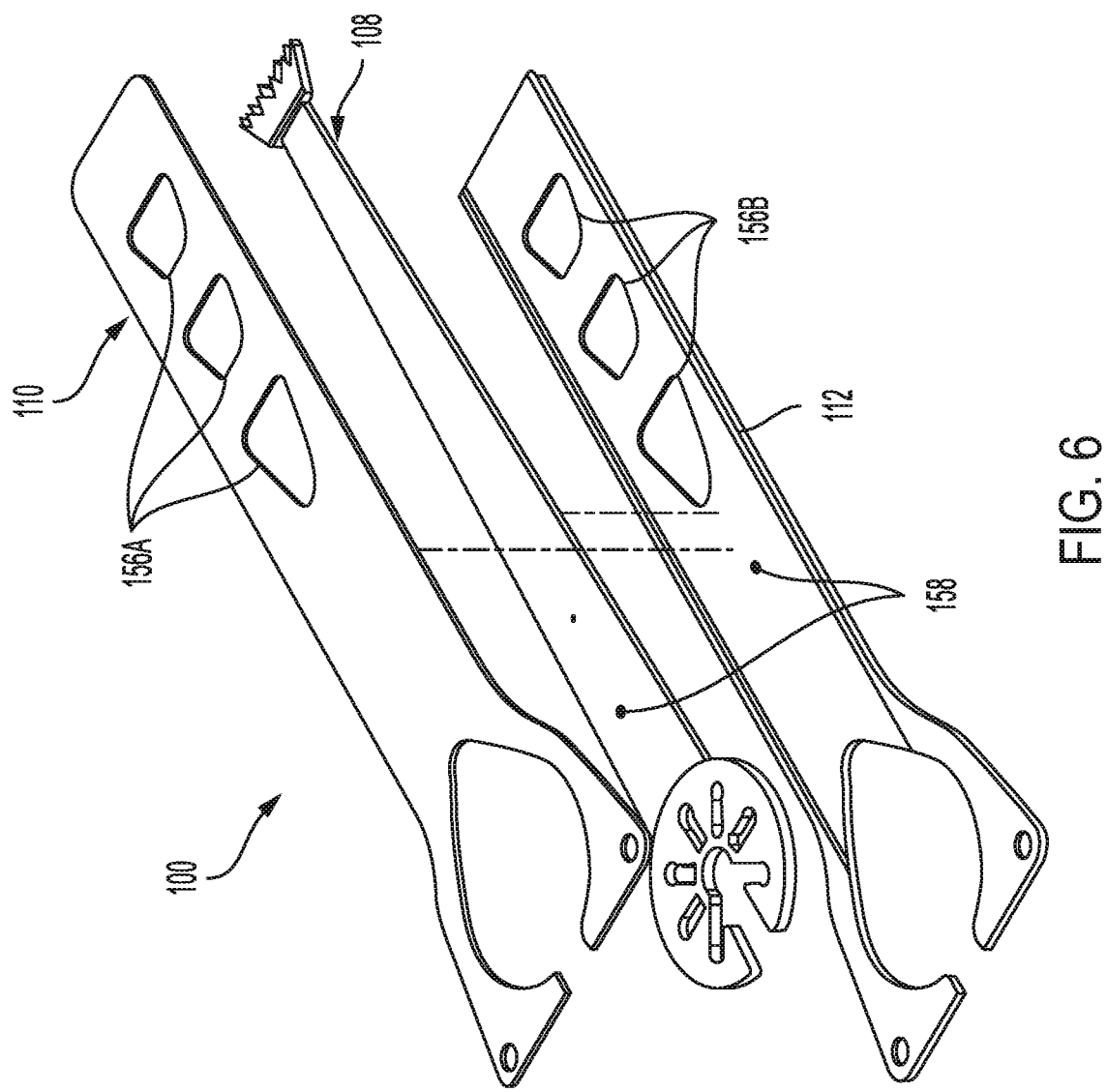
FIG. 6 is an exploded perspective view schematic representation of the sheathed blade assembly, according to an alternative embodiment.

Turning now to FIGS. 5 and 6, there are shown top perspective and exploded perspective views schematic representations of the sheathed blade assembly 100, according to an alternative embodiment. In the alternative embodiment of the sheathed blade assembly 100 shown in FIGS. 5 and 6, the exterior sheath 106 comprises a plurality of cutouts 146 (i.e., apertures or openings). As shown in FIG. 5, the top portion 110 of the exterior sheath 106 comprises three trapezoid-shaped or triangular cutouts 156A extending therethrough. However, any number of cutouts 156A of any shape or configuration can be used.

In FIG. 6, the bottom portion 112 of the exterior sheath 106 additionally comprises a plurality of cutouts 156B (i.e., apertures or openings) extending therethrough. The bottom portion 112 of the exterior sheath 106 also comprises three trapezoid-shaped or triangular cutouts 156B extending therethrough (although any number of cutouts 156B of any shape or configuration can be used as well). In the depicted embodiment, the cutouts 156B in the bottom portion 112 of the exterior sheath 106 are aligned within the cutouts 156A in the top portion 110 of the exterior sheath 106. The cutouts 156A, 156B reduce the surface area of contact between the interior blade 108 and the exterior sheath 106 and allow fluid from the surgical site to lubricate the moving parts. Thus, the cutouts 156A, 156B reduce friction and wear within the sheathed blade assembly 100, reducing heat and metal particulate generation of the sheathed blade assembly 100. To further reduce friction, wear, and heat, any surfaces of the interior blade 108 and the exterior sheath 106 may also comprise a coating 158, such as physical vapor deposition (PVD) coatings, diamond-like carbon coatings, and/or dry lubricating coatings, such as tungsten disulfide.

Referring now to FIG. 7, there is shown a side perspective view schematic representation of a universal saw head 160, according to an embodiment. In the depicted embodiment, the saw head 160 comprises a collet 162 (with an opening 170) for accommodating both sheathed blade assemblies 100 (FIG. 1) and non-sheathed (standard) blades 200. When using sheathed blades 100, as shown in FIGS. 1-2, the collet 162 secures the exterior sheath 106 in order to keep it stationary, while the interior blade 108 is engaged and driven using the hub 164 of the interior blade 108. When using non-sheathed blades 200, the saw head 160 engages and drives the non-sheathed blade 200 using the hub (not shown) of the non-sheathed blade 200 because it has the same structure of the hub 164 of the sheathed blade assembly 100 (FIG. 2), while the collet 162 provides sufficient clearance such that the standard blade 200 will not contact any of the mechanisms associated with securing the exterior sheath 106. As the saw head 160 can accommodate both sheathed blade assemblies 100 (FIG. 1) and non-sheathed (standard) blades 200, it eliminates the need for two different types of saw handpieces, reducing purchase costs and inventory. It also improves logistics for hospitals and surgical centers. A single universal saw head 160, as shown in FIG. 7, also provides a user (e.g., surgeon) greater flexibility in the choice of blade types for various surgical resections during an orthopedic procedure.

Figure 8:
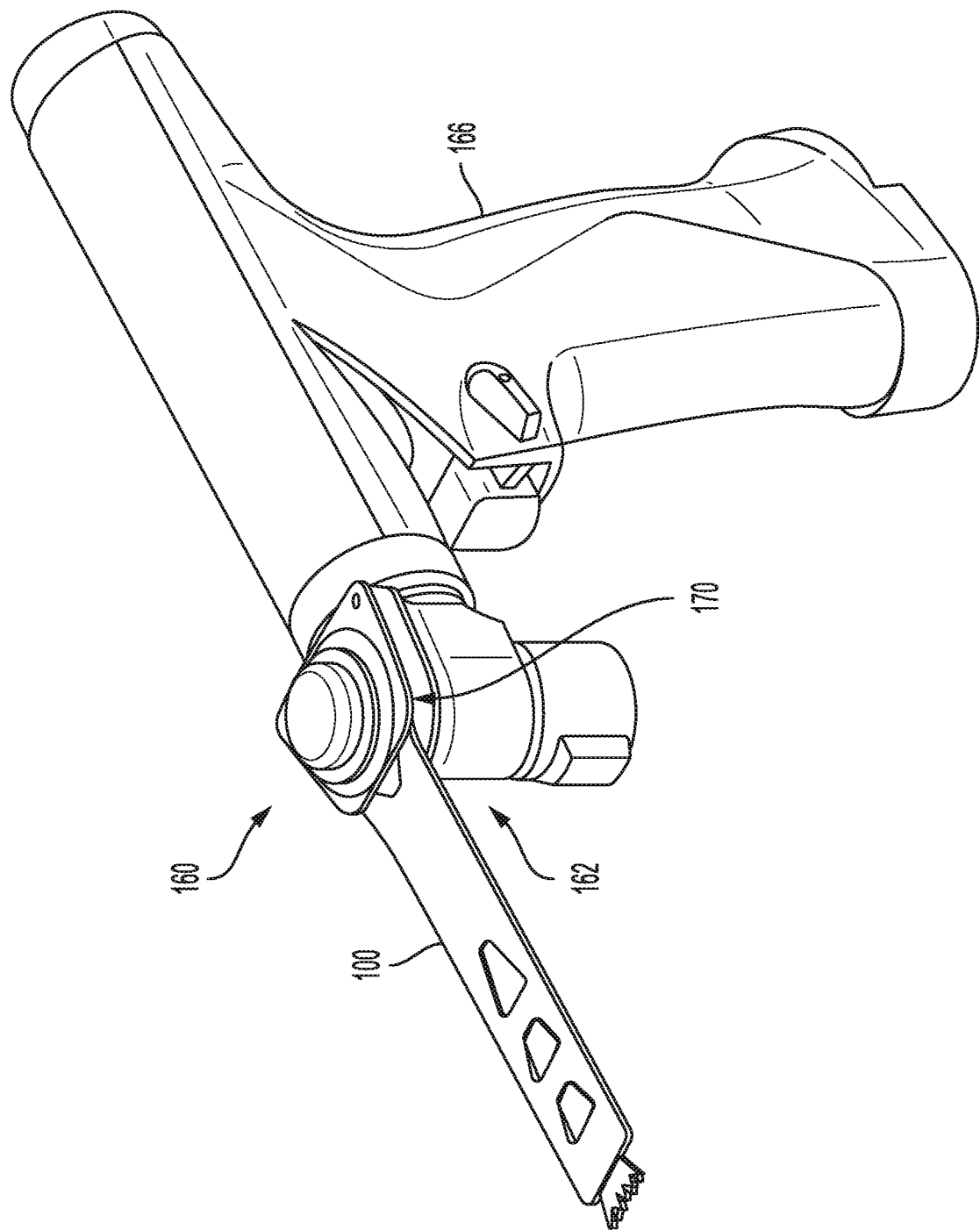
FIG. 8 is a side perspective view schematic representation of a sheathed blade assembly connected to the universal saw head, according to an embodiment.
Figure 9:
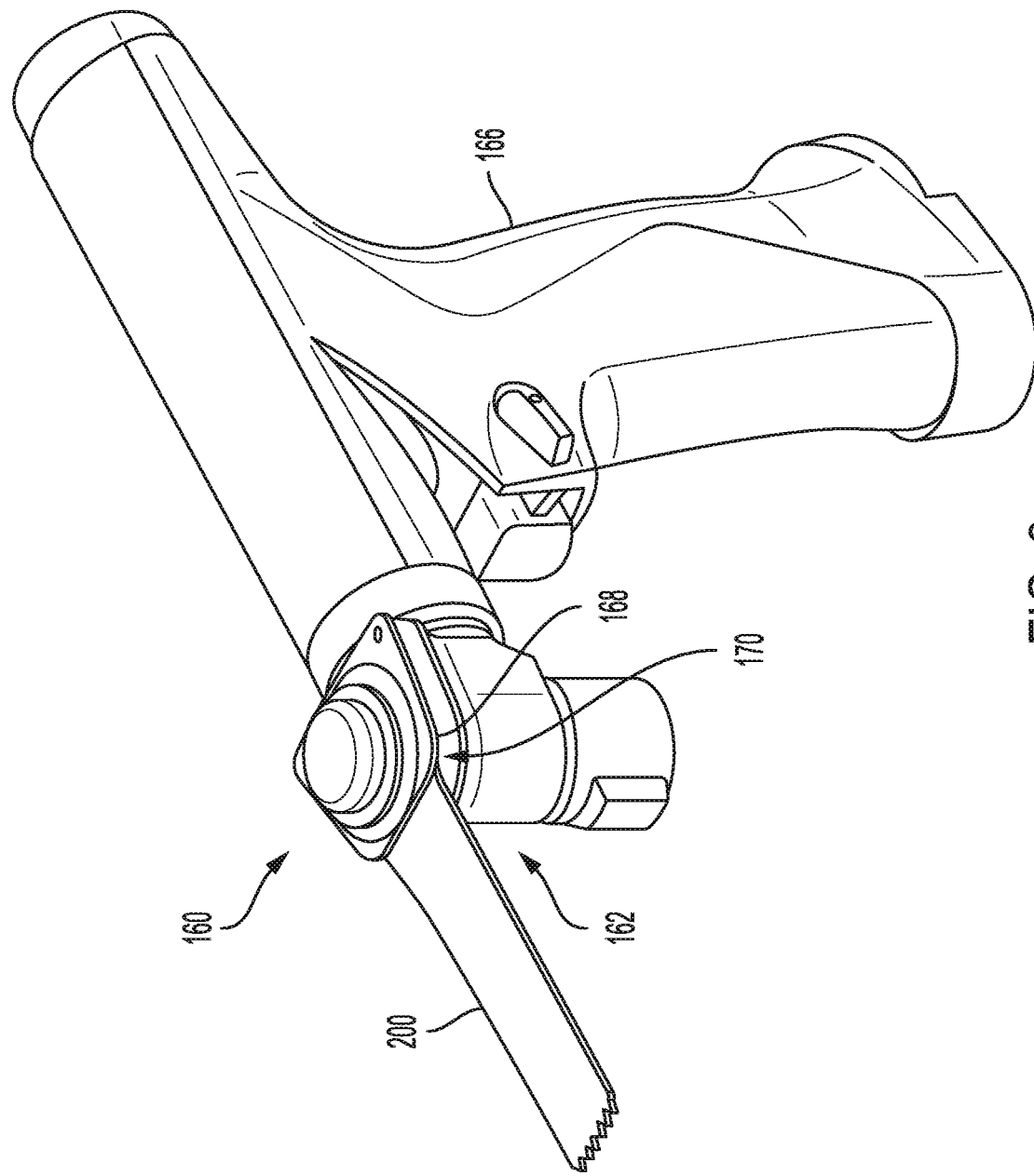
FIG. 9 is a side perspective view schematic representation of an non-sheathed blade connected to the universal saw head, according to an alternative embodiment.

Turning briefly to FIGS. 8 and 9, there are shown side perspective views schematic representations of a sheathed blade assembly 100 and non-sheathed blade 200, respectively, connected to the universal saw head 160. As shown in both FIGS. 8 and 9, the universal saw head 160 of FIG. 7 can be attached to handpiece 166. The handpiece 166 can be any handpiece with a drive mechanism, such as a battery operated handpiece or a pneumatic handpiece.

In FIG. 8, an embodiment wherein the sheathed blade assembly 100 is used, the collet 162 grabs the arms 126 at the distal end 122 of the bottom portion 112 of the exterior sheath 106 (FIG. 2). In particular, as shown in FIG. 10, one or more raised areas 172 on the collet 162 clamp (or otherwise grab) the exterior sheath 106 of the sheathed blade assembly 100 to hold it stationary while the interior blade 108 essentially floats within the exterior sheath 106. Thus, the collet 162 connects to the stationary exterior sheath 106 without contacting the movable interior blade 108, as also shown in FIG. 10.

When the non-sheathed (standard) blade 200 is used, as shown in FIG. 9, the collet 162 connects to the hub (similar to the hub 164 of the sheathed blade assembly 100 (FIG. 2)) of the non-sheathed blade 200 but leaves a clearance amount 168 between the blade 200 and the collet 162 in order to prevent contact, heat, and damage. The clearance amount 168 in FIG. 9 can be created by a recess 174 in the collet 162, such as that shown in FIG. 10. The recess 174 provides the clearance amount 168 (FIG. 9) between the collet 162 and the non-sheathed blade 200.

FIG. 10 also shows various other components of the collet 162 and saw head 160. In the depicted embodiment, the sheathed blade assembly 100 is attached to the collet 162 (and saw head 160) via a cap 176 and a conventional connector 178. In the depicted embodiment, the connector 178 is attached to the cap 176 and extends through the hub 164 of the sheathed blade assembly 100 and the collet 162. As also shown in FIG. 10, the saw head 160 comprises a driving hub 180. The driving hub 180 is a movable component of the saw head 160. When the stationary exterior sheath 106 is clamped by the raised areas 172 of the collet 162, the interior blade 180 is driven, moved, or otherwise actuated by the driving hub 180, which is connected to the driving mechanism (not shown) in the handpiece 166.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A sheathed blade assembly, comprising:
   an exterior sheath having a top portion and a bottom portion with an inner lumen therebetween;
   an interior blade movable within the inner lumen of the exterior sheath;
   a ball bearing within the inner lumen of the exterior sheath;
   wherein the ball bearing creates a clearance amount between the interior blade and at least one of the top portion and the bottom portion of the exterior sheath.

2. The assembly of claim 1, wherein the exterior sheath is stationary relative to the movable interior blade.

3. The assembly of claim 1, wherein the interior blade is tapered toward a proximal cutting end.

4. The assembly of claim 3, further comprising a head at the proximal cutting end of the interior blade, the head having a plurality of cutting teeth extending therefrom.

5. The assembly of claim 4, wherein the head has a width that increases proximally.

6. The assembly of claim 1, wherein the interior blade has a distal connecting end including a circular disk having a plurality of apertures extending therethrough.

7. The assembly of claim 6, further comprising an opening extending into the circular disk.

8. The assembly of claim 7, wherein the bottom portion of the exterior sheath comprises a distal end with an opening aligned with the opening in the circular disk.

9. A sheathed blade assembly, comprising:
   an exterior sheath having a first portion and a second portion with an inner lumen therebetween;
   an interior blade movable within the inner lumen of the exterior sheath;
   a first pocket within a first surface of the interior blade;
   a first ball bearing within the first pocket;
   wherein the first ball bearing creates a clearance amount between the first surface of the interior blade and the first portion of the exterior sheath.

10. The assembly of claim 9, further comprising a second pocket within a second surface of the interior blade, the second surface opposing the first surface.

11. The assembly of claim 10, further comprising a second ball bearing within the second pocket.

12. The assembly of claim 11, wherein the second ball bearing creates a clearance amount between the second surface of the interior blade and the second portion of the exterior sheath.

13. The assembly of claim 10, wherein the second pocket is in a staggered configuration relative to the first pocket.

14. The assembly of claim 9, further comprising a first plurality of cutouts extending through the first portion.

15. The assembly of claim 14, further comprising a second plurality of cutouts extending through the second portion, the second plurality of cutouts aligned with the first plurality of cutouts.

16. The assembly of claim 9, further comprising a coating on at least one of the interior blade and the exterior sheath, the coating composed of at least one of a physical vapor deposition (PVD) coating, a carbon coating, and a dry lubricating coating.

17. A surgical saw, comprising
    a saw head comprising a collet extending along a longitudinal axis with an opening configured to receive a movable blade;
    wherein the blade is removably connected within the collet;
    a clearance amount positioned between the collet and the blade by a recess in the collet;
    a handpiece connected to the saw head, the handpiece having a drive mechanism; and
    wherein the drive mechanism moves the blade, wherein the movable blade comprises a stationary exterior sheath with a pair of arms.

18. The surgical saw of claim 17, wherein the pair of arms connect the movable blade within the collet.

* * * * *

UNITED STATES PATENT AND TRADEMARK OFFICE
CERTIFICATE OF CORRECTION

PATENT NO. : 11,812,973 B2
APPLICATION NO. : 16/977345
DATED : September 1, 2020
INVENTOR(S) : John Sieh and David Gonzalez It is certified that error appears in the above-identified patent and that said Letters Patent is hereby corrected as shown below:

In the Claims

Column 8, Line 47, Claim 17, please add the word "created" between "blade" and "by"

Signed and Sealed this
Thirteenth Day of August, 2024

Katherine Kelly Vidal
*Director of the United States Patent and Trademark Office*